US006344052B1

(12) United States Patent
Greenan et al.

(10) Patent No.: US 6,344,052 B1
(45) Date of Patent: Feb. 5, 2002

(54) TUBULAR GRAFT WITH MONOFILAMENT FIBERS

(75) Inventors: Trevor Greenan, Miami; Howard Leonhardt, Weston, both of FL (US)

(73) Assignee: World Medical Manufacturing Corporation, Sunrise, FL (US)

( * ) Notice: Subject to any disclaimer, the term of this patent is extended or adjusted under 35 U.S.C. 154(b) by 0 days.

(21) Appl. No.: 09/406,981

(22) Filed: Sep. 27, 1999

(51) Int. Cl.[7] ................................................. A61F 2/06
(52) U.S. Cl. ...................... 623/1.1; 623/1.35; 623/1.33; 623/1.25
(58) Field of Search ............................... 606/194; 623/1, 623/1.3 J, 1.5, 1.51, 1.53, 1.11, 1.33

(56) References Cited

U.S. PATENT DOCUMENTS

| | | |
|---|---|---|
| 4,580,568 A | 4/1986 | Gianturco |
| 4,655,771 A | 4/1987 | Wallsten |
| 4,878,906 A | 11/1989 | Lindemann et al. |
| 4,954,126 A | 9/1990 | Wallsten |
| 5,108,224 A | 4/1992 | Cabaniss et al. |
| 5,156,619 A * | 10/1992 | Ehrenfeld ........................ 623/1 |
| 5,236,447 A | 8/1993 | Kubo et al. |
| 5,282,848 A | 2/1994 | Schmitt |
| 5,342,348 A | 8/1994 | Kaplan |
| 5,507,771 A | 4/1996 | Gianturco |
| 5,527,353 A | 6/1996 | Schmitt |
| 5,618,301 A | 4/1997 | Hauenstein et al. |
| 5,741,332 A | 4/1998 | Schmitt |
| 5,800,510 A | 9/1998 | Schmitt |
| 5,911,753 A | 6/1999 | Schmitt |
| 6,042,592 A | 3/2000 | Schmitt |
| 6,099,557 A | 8/2000 | Schmitt |
| 6,123,723 A * | 9/2000 | Konya et al. ............... 623/1.11 |

FOREIGN PATENT DOCUMENTS

EP          0 855 170          7/1998

OTHER PUBLICATIONS

Williams, David F., Biocompatibility of Clinical Implant Materials, Chapter 8, pp. 177–209, *Polyethylene Terephthalate (Dacron®) Vascular Prostheses–Material And Fabric Construction Aspects*, CRC Press, 1981.

* cited by examiner

*Primary Examiner*—Henry J. Recla
*Assistant Examiner*—Vy Q. Bui
(74) *Attorney, Agent, or Firm*—Sterne, Kessler, Goldstein & Fox P.L.L.C.

(57) ABSTRACT

A thin-walled prosthesis is provided that includes a tubular graft formed of a monofilament fiber. The graft has sufficient strength and durability to withstand loads applied during deployment and while implanted and sufficiently low permeability to prevent excessive leakage of body fluids through the material or to provide a sufficient seal, for example, so as to prevent aneurysm pressurization. A preferred embodiment of the present invention relates to a tubular grafts constructed of monofilament fibers for endoluminal placement within a body lumens, including blood vessels, and for the treatment of abdominal and other aneurysms.

21 Claims, 2 Drawing Sheets

TUBULAR GRAFT WITH MONOFILAMENT FIBERS

FIELD OF THE INVENTION

The present invention relates to tubular prostheses such as grafts and endoluminal prostheses including, for example, stent-grafts and aneurysm exclusion devices, and methods for placement of such grafts and endoluminal structures. More particularly, the present invention relates to a graft or a prosthetic device including a graft constructed of monofilament fibers for placement within or in place of a body lumen, including, for example, vascular grafts for replacing blood vessels, devices for opening or supporting blood vessels, and devices for the treatment of abdominal and other aneurysms.

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

Also a number of vascular grafts have been developed for either replacing, supplementing or excluding portions of blood vessels. These vascular grafts may include but are not limited to endoluminal vascular prostheses.

Graft materials have been used in a number of medical applications including in vascular graft and/or in endoluminal prostheses. Among other applications, materials have been used in tubular vascular prostheses for repairing or replacing blood vessels. They have also been used in aneurysm exclusion devices such as abdominal aortic aneurysm ("AAA") devices that are used to exclude aneurysms and provide a prosthetic lumen for the flow of blood. Further uses have included stent-grafts such as covered stents that are used for providing artificial radial support to the wall tissue, which forms the various lumens in the body. Such covered stents have attempted among other things to address problems that are presented by a thrombogenic environment or to promote healing in the vessel wall tissue that is prone to scarring. These attempts include providing a lining or covering in conjunction with an implanted stent. Typically graft materials used in these include multifilament woven polymer materials and polytetrafluoroethylene ("PTFE"). The stent-grafts may have graft material on the inner diameter or outer diameter of a support structure.

One very significant of these uses for endoluminal or vascular grafts is in treating aneurysms.

Vascular aneurysms are the result of abnormal dilation of a blood vessel, usually resulting from disease or genetic predisposition which can weaken the arterial wall and allow it to expand. While aneurysms can occur in any blood vessel, most occur in the aorta and peripheral arteries, with the majority of aneurysms occurring in the abdominal aorta. Typically an abdominal aneurysm will begin below the renal arteries and may extend into one or both of the iliac arteries.

Aneurysms, especially abdominal aortic aneurysms, have been most commonly treated in open surgery procedures where the diseased vessel segment is bypassed and repaired with an artificial vascular graft. While considered to be an effective surgical technique in view of the alternative of a fatal ruptured abdominal aortic aneurysm, the open surgical technique suffers from a number of disadvantages. The surgical procedure is complex and requires long hospital stays due to serious complications and long recovery times and has high mortality rates.

In order to reduce the mortality rates, complications and duration of hospital stays, less invasive devices and techniques have been developed. The improved devices include tubular prostheses that provide a lumen or lumens for blood flow while excluding blood flow to the aneurysm site. The prostheses are typically made of a tubular multifilament woven graft material that is secured to a vessel wall above and below the aneurysm site with at least one attached expandable ring member that provides sufficient radial force so that the prosthesis engages the inner lumen wall of the body lumen. Other mechanisms have been used to engage the vessel walls such as, for example, forcibly expandable members or hook like members that puncture the vessel wall.

Although frequently referred to as stent-grafts, these devices differ from covered stents in that they are not used to mechanically prop open natural blood vessels. Rather, they are used to secure an artificial lumen to the vessel wall without further opening the natural blood vessel that is already abnormally dilated.

These aneurysm exclusion devices are preferably loaded into a catheter, which is used to deliver and place the prosthesis at an appropriate location. This has been done one of several ways. Most frequently, a surgical cut down is made to access a femoral iliac artery. The catheter is then inserted into the artery and guided to the aneurysm site using fluoroscopic imaging where the device is released from the catheter. Where expandable rings are used, the rings supporting the graft, biased in a radially outward direction, then expand to engage the prosthesis in the vessel against the vessel wall to provide an artificial lumen for the flow of blood. Another technique, though less frequently used, includes percutaneously accessing the blood vessel for catheter delivery, i.e., without a surgical cutdown.

Multifilament fibers have been used in AAA devices, primarily because it was believed that the fibers provide relative strength and durability required by the prostheses and monofilament fiber based grafts have been avoided because they had insufficient leak resistance. Typically the woven multifilament graft material is made of yarns which consist of about 25 to 100 fibers. The selection of yarn dictates the resultant mechanical properties such as percent elongation, fatigue strength, burst strength, and permeability to water or other fluids. One disadvantage to using these materials is that the multifilament fiber adds bulk, and relatively bulky grafts are more difficult to deliver using modem low-profile endovascular techniques. Another disadvantage is that they cannot be woven into fabric without a significant number of fissures or hooks (frays) and defects that occur during the weaving process. These fissures, hooks and defects tend to make the woven graft material even thicker and may cause increased tissue immune response. Lower profile multifilament woven materials have not provided sufficient strength to the grafts in which they have been used.

One disadvantage of the currently used devices is that when radially compressed, they are larger than would be ideal and thus require larger diameter catheters for delivery.

This makes catheter access to the site and maneuverability through the tortuous or narrowed diseased vessels more difficult and may exclude some patients from eligibility for some procedures. In most current AAA devices, the total outer diameter of the introducer systems are relatively large, i.e., around 20–24 French. Providing a smaller introducer system would, among other things, allow for treatment of patients with smaller blood vessel diameters and provides for faster delivery.

Therefore, it is desirable to provide an endoluminal graft that is made of a material having sufficient strength, durability and low-permeability, while capable of being radially compressed into and delivered from smaller diameter delivery catheters.

SUMMARY OF THE INVENTION

The present invention provides an improved endoluminal prosthesis made of a graft material having a relatively smaller collapsed profile. In particular, the present invention provides an endoluminal graft device made of monofilament fibers instead of the fiber bundles of the multifilament fibers. Accordingly the present invention provides for a lower volume structure with comparable strength. More particularly, the graft material comprises a finely woven monofilament fiber with a small enough pore size and low enough percent open area to provide thin graft material with low permeability. The monofilament fibers may be woven in a number of ways as are generally known in the art to provide more densely packed material and smaller pore sizes. In one preferred embodiment, the material is woven polyester. The monofilament fibers may be shaped in a manner to provide a more compact and stronger material. For example, the fibers may be rounded or oval in shape.

The graft material is of a sufficiently low permeability so as to avoid excessive leakage, to prevent pressurization of the aneurysm and/or to form a seal. Although some leakage of blood or other body fluid may occur into the aneurysm site isolated by the prosthesis, the graft material is believed to prevent the pressurization of the aneurysm and thus aneurysm rupture. It is believed that by preventing excessive leakage into the aneurysm site the chance of pressurization of the aneurysm will be significantly decreased. In other words, by isolating the aneurysm from the flow of blood through the blood stream, aneurysm rupture is prevented. Permeability of the graft, in part, determines whether or not excessive or clinically undesirable leakage will occur through the graft material. Preferably the water permeability of the graft is at about 2300 ml/cm$^2$/min or less and most preferably at about 600 ml/cm$^2$/min or less.

Another important parameter in constructing a graft is the material thickness. The thickness of the material is sufficiently low to allow the endoluminal graft to collapse to a small enough profile to allow placement into the vasculature. The graft is thus thin-walled so that is may be compressed into a small diameter catheter, yet capable of acting as a strong, leak-resistant, fluid conduit when in tubular form. The present invention in the embodiment of an AAA device would enable smaller French size introducer systems, i.e., to sizes of 18 French or less. Preferably the wall thickness is in the range of 80 microns or less.

The strength of the material is sufficient to allow it to withstand the loads applied during deployment and the cyclical loading in the body for a reasonable duration. Where an annular support structure or stent is used, the endoluminal graft must provide sufficient strength to allow attachment of the annular support structure or the stent.

Preferably the graft material has a pore size of 11 microns or less, a percent open area of about 5% or less, and/or a tensile strength of about 44 pounds per inch, most preferably a pore size of about 5 micron or less, a percent open area of about 1% or less and a tensile strength of about 65 pounds per inch or less. A suitable material would be a polyester.

A preferred embodiment of the present invention relates to a tubular grafts constructed of monofilament fibers for endoluminal placement within a body lumens, including blood vessels, and for the treatment of abdominal and other aneurysms. This embodiment of the tubular graft includes radially compressible annular spring portions which when released, bias the proximal and distal portions of the graft into conforming fixed engagement with an interior surface of the vessel.

One embodiment provides an aneurysm repair system characterized by a graft apparatus which can be placed within a diseased vessel via deployment means at the location of an aneurysm. The graft device comprises a tubular graft formed of a woven monofilament fiber for conducting fluid. The graft device may be in the form of either a straight single-limb graft or a generally Y-shaped bifurcated graft having a trunk joining at a graft junction with a pair of lateral limbs, namely an ipsilateral limb and a contralateral limb. Preferably the ipsilateral limb is longer so that when deployed, it extends into the common iliac. A single limb extension graft is provided having a mating portion for coupling with a lateral limb of a bifurcated graft and an adjustable length portion extending coaxially from a distal end of the mating portion.

The graft apparatus includes radially compressible spring means having at least two coaxially spaced annular portions for biasing the proximal and distal portion of an associated graft limb or limb portion radially outward into conforming fixed engagement with the interior of the vessel. The annular portions are preferably constructed of nitinol. Examples of such spring means are described, for example, in U.S. Pat. Nos. 5,713,917 and 5,824,041 incorporated herein by reference.

In the extension graft, an annular spring portion is located at a distal end of the adjustable length portion for similar biasing purposes. The proximal portion of the extension graft includes a spring means for engaging the inner lumen of the contralateral limb portion of the graft.

The spring means may be attached to the graft by various means, such as, for example, by stitching the annular portions on either the inside or outside of the tubular graft.

Various means for deployment of the devices are well known in the art and may be found for example is U.S. Pat. Nos. 5,713,917 and 5,824,041 which are incorporated herein by reference. In general, the graft is radially compressed and loaded into a catheter. The aneurysm site is located using an imaging technique such as fluoroscopy and is guided through a femoral iliac artery with the use of a guide wire to the aneurysm site. Once appropriately located, the sheath on the catheter covering the tubular graft is retracted, thus allowing the annular springs to expand and attach or engage the tubular graft to the inner wall of the body lumen.

DETAILED DESCRIPTION OF THE PREFERRED EMBODIMENTS

Figure 1:
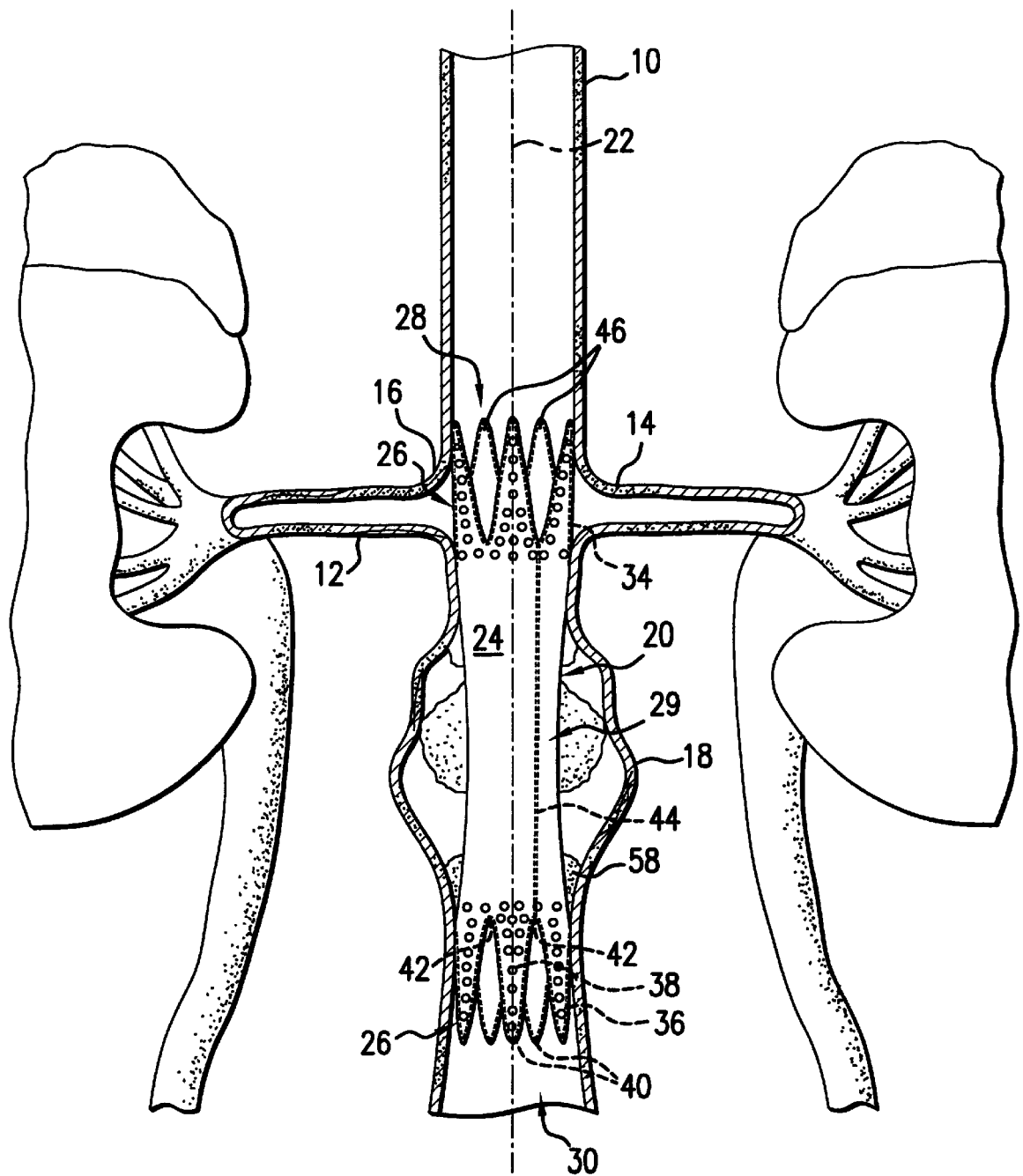
FIG. 1 is an elevational view showing a single-limb graft of the present invention fully deployed within an aorta of a patient to repair an aneurysm.

In a preferred embodiment, a monofilament graft material is made into vascular grafts by sewing the material into single tubular structures. Seams are sewn with a Locking stitch with 5–0 size suture material (Ethibond PN 8890H). Then, annular nitinol support structures are sewn into the graft material in a manner as described with respect to the embodiments referred to in FIGS. 1 and 2.

Specific graft materials are selected based on performance criteria such as pore size, percent open space, water permeability, wall thickness, tensile strength, and strength per stitch.

Two examples of suitable materials based on these selection criteria are as follows:

EXAMPLE 1

The Medifab™ 7-11/5 material manufactured by Tetko, Inc., now Sefar America, Inc. was selected based on these parameters. The specification of the material provides a pore size 11 microns and a 5% open area. One manner in which pore size and open area may be determined is by taking images of the graft materials on suitable equipment such as a Scanning Electron Microscope, SEM. Measurements are made of the width of the fibers. Open area of the mesh is then measured in each direction and used to determine pore size, and based on the total graft area, the percent open area. The specified product thickness of about 60 microns was confirmed to be approximately correct. A tensile strength of about 45 per inch, and a seam strength of over 13 lbs. per inch were also measured where the seam stitching was on average at a rate of 19 stitches per inch.

The water permeability of the material was measured at approximately between 2100–2300 ml/cm$^2$/min. Permeability testing was determined by supplying filtered water at 120 mm Hg to a circular aperture (between 1 and 0.5 cm$^2$) containing the sample and collecting the flow. The permeability is calculated from the equation: water permeability= Q/A where Q is the flow rate through the sample in mL/min and A is the cross-sectional area of the aperture in cm$^2$. The testing is based on ANSI/AAMI VP20-1994 section 8.2.2 "Method for determination of water permeability." Some exceptions to the testing protocol were it did not meet the specification that "there are no bends or changes in diameter of flow pathway within a distance from the test sample of six diameters of the test area." Also, some testing was run for 30 seconds instead of 60 seconds.

The material was woven using a 2/2 Twill weave using fibers having a diameter of about 38 microns. The grafts were implanted in animals in studies and were found to have no excessive leakage.

The material was also found to have a strength of at least 48 lbs. per inch and at least comparable or lower permeability when the material was treated by a calendaring process where the material is heated below the melting point and pressed. The calendaring process reduced the thickness of the material from about 60 microns to about 40 microns, i.e., about a 30% reduction in material thickness. This process may also be used to make the material less permeable.

EXAMPLE 2

The Medifab™ 7-5/1 material manufactured by Tetko, Inc., now Sefar America Inc. were selected based on parameters described above. The material specifications provide a pore size of 5 micron and a 1% open area. The specified product thickness is about 80 microns. A tensile strength of about 68 lbs. per inch, and a seam strength of over 35 lbs. per inch were also measured where the seam stitching was on average at a rate of 19 stitches per inch. The water permeability of the material has been measured at approximately between 400 ml/cml/min and 600. The material is woven using a 4/4 Twill weave with fibers having a diameter of about 34 microns. The grafts were implanted in animals in studies and were found to have no excessive leakage.

Referring now to FIG. 1, there is illustrated the monofilament graft of the present invention in use with an aneurysm exclusion device.

The device is shown in place in an abdominal aorta. An aorta 10 is joined by renal arteries 12 and 14 at the aorto-renal junction 16. Just below the aorta-renal junction is an aneurysm 18, a diseased region where the vessel wall is weakened and expanded. An elongated single-limb tubular prosthesis 20 is deployed at the region of aneurysm 18 for the purpose of relieving blood flow pressure against the weakened vessel wall by acting as a fluid conduit through the region of the aneurysm. In its deployed condition, prosthesis 20 defines a central longitudinal axis 22 extending in a direction of blood flow through aorta 10.

Prosthesis 20 comprises a graft material 24 enclosing radially compressible spring means 26 for biasing a proximal end 28 and a distal end 30 of the prosthesis into conforming fixed engagement with an interior surface of aorta 10.

Graft material 24 is a biocompatible, low-porosity fabric, woven from a monofilament fiber such as polyester. The graft 24 is thin-walled so that is may be compressed into a small diameter catheter, yet capable of acting as a strong, leak-resistant, fluid conduit when in tubular form. Monofilament fibers are interwoven to form the graft material 24. The graft material 24 is formed into a tube as illustrated.

A middle portion 29 of prosthesis 20 between proximal end 28 and distal end 30 is tapered to provide a decreased fluid-conducting cross-sectional area relative to ends 28 and 30, such as by excising at least one longitudinal strip of graft material 24 and sewing the resulting gap or gaps closed, as a way of reducing the occurrence of folding and wrinkling and adapting the graft to fit within a wider range of differently sized vessels.

Enclosed within graft material 24 is a nitinol wire spring having a proximal spring portion 34 and a distal spring portion 36. Alternatively, the proximal spring portion 34 may have uncovered portions or open areas proximal of the graft material so that in the event the spring portion 34 is deployed over the renal arteries 12, 14, the blood flow through arteries 12, 14 will not be blocked. Spring portions 34 and 36 are designed to exert radially outward force sufficient to bias graft material 24 at graft ends 28 and 30 into conforming fixed engagement with the interior surface of aorta 10 above and below aneurysm 18. The nitinol wire used to form the spring is in a superelastic, straight annealed condition and may be coated with titanium oxide to improve biocompatibility, reduce the incidence of allergic reaction to nickel, and improve radiopacity. Other coatings as are generally known in the art may also be used to lower the risks of blood clotting and wire corrosion. Spring portions 34 and 36 are each formed by revolving a sinusoidal wire pattern of straight spokes 38 connected by rounded alternating crests 40 and troughs 42 about central axis 22 to provide a continuous annular spring portion. A preferred spring portion includes five equispaced crests 40 and five equispaced troughs 42 formed to a predetermined radius to produce better spring properties and avoid sharp transitions in the wire, in that sharp transitions are more prone to failure. The coaxially spaced spring portions 34 and 36 are connected by at least one straight connecting bar 44 which preferably extends generally parallel to central axis 22 for minimal disruption of blood flow. Connecting bar 44 provides torsional stability for graft 20, and may be welded to spring portions 34 and 36, or fastened thereto by a small, tightened sleeve (not shown).

The wire spring is sewn within graft material 24 using a polyester suture. A preferred stitch pattern includes two generally parallel stitches extending along opposite sides of the wire, and a cross-over stitch around the wire for pulling the parallel stitches together to achieve tight attachment of graft material 24 to the wire spring. This method of attachment substantially prevents contact between wire spring and the interior surface of the vessel, and is reliable over time. In accordance with the present invention, graft material 24 may be cut out between crests 40 of proximal spring portion 34 and distal spring portion 36 to define a plurality of radially distensible finger portions 46 at graft ends 28 and 30. Importantly, finger portions 46 allow graft 20 to be situated with proximal end 28 relatively close to aorto-renal junction since gaps between the finger portions may be aligned with renal arteries 12 and 14 so as not to block blood flow. Finger portions 46 may be radially compressed to approximate a conical tip to facilitate loading insertion of prosthesis 20 within a sheath.

The prosthesis 20 may be loaded into a catheter and delivered via catheter through a surgically accessed femoral artery, to the desired deployment site. These and suitable delivery methods and apparatus are generally known in the art and may be used to deliver the prosthesis. An example of such technique is set forth in U.S. Pat. No. 5,713,917, incorporated herein by reference.

A bifurcated prosthesis 60 as shown in FIG. 4 is also within the scope of the present invention for use in cases where involvement of one or both iliac vessels 11 and 13 is indicated. Prosthesis 60 is Y-shaped and includes a primary limb 62 for location within aorta 10, and is joined by an ipsilateral limb 64 for location within ipsilateral iliac vessel 11, and by a contralateral limb 66 for location within contralateral iliac vessel 13, at a graft junction 63. Each limb of bifurcated prosthesis 60 is generally similar in construction to single-limb prosthesis 20. They are made of monofilament fiber graft material 24. Proximal and distal ends of each limb are biased into conforming fixed engagement with the interior surface of a corresponding vessel by annular spring portions associated therewith, and middle portions of each limb are preferably tapered. A first nitinol wire spring is enclosed by, and attachably sewn within, graft material 24 and includes a proximal spring portion 68A associated with a proximal end of primary limb 62, a distal spring portion 68B associated with a distal end of primary limb 62, and an axially extending connecting bar 68C coupling the proximal and distal spring portions together. Similarly, a second nitinol wire spring having a proximal spring portion 70A, a distal spring portion 70B, and an axially extending connecting bar 70C, is sewn within ipsilateral limb 64; and a third nitinol wire spring having a proximal spring portion 72A, a distal spring portion 72B, and an axially extending connecting bar 72C, is sewn within contralateral limb 66. Terminal ends of bifurcated graft 60, namely the proximal end of primary limb 62 and the distal ends of lateral limbs 64 and 66, are provided with radially distensible finger portions 46 as described above. Where entry is to be made through an ipsilateral femoral artery to deploy prosthesis 60, distal spring portion 72B is held in a radially compressed condition by an expandable retainer ring 79, which may simply be a length of suture material tied end to end using a purse-string type knot to form a loop, to prevent premature deployment of distal spring portion 72B prior to proper positioning thereof within contralateral iliac vessel 13. Likewise, where entry is to be made through a contralateral femoral artery, distal spring portion 70B may be provided with a retainer ring 79 to prevent premature deployment of distal spring portion 70B prior to proper positioning thereof within ipsilateral iliac vessel 11.

Although this detailed description sets forth a particular and preferred embodiment, it is to be understood that the claimed invention is not limited to this particular embodiment. The present invention contemplates various other vascular grafts or endoluminal prostheses in which a monofilament material is used, such as, for example, forcibly expanded coronary and peripheral stents or stent-grafts, covered grafts, vascular grafts, and other aneurysm exclusion devices. The expandable support structures on various embodiments of the devices may be, for example, self-expanding, balloon expandable, or otherwise forcibly expanded. Other biologically compatible materials formed into monofilament fibers are contemplated, including other polymers that may be woven into graft materials.

What is claimed is:

1. A vascular graft for use within a human body comprising:
   a graft material constructed from interwoven monofilament fibers;
   wherein said graft material has an average pore size of about 11 microns or less.

2. The vascular graft of claim 1 wherein said graft material has a water permeability of about 2300 m/cm$^2$/min or less.

3. The vascular graft of claim 1 wherein said graft material has a water permeability of about 600 ml/cm$^2$/min or less.

4. The vascular graft of claim 1, wherein said graft material has a percent open area of about 5 percent or less.

5. The vascular graft of claim 1 wherein said graft material has a substantially uniform wall thickness of about 80 microns or less.

6. The vascular graft of claim 1, wherein said graft material has an average pore size of less than about 5 microns.

7. The vascular graft of claim 1 wherein said graft material has a tensile strength of at least 44 pounds per inch.

8. The vascular graft of claim 1 wherein said graft material has a wall thickness of about 60 microns or less.

9. The vascular graft of claim 1 wherein said graft material is treated by pressing and heating said graft material.

10. The vascular graft of claim 1 wherein said monofilament graft material has a proximal portion having a proximal opening and a distal portion having a distal opening, said openings and said graft material forming a lumen for the flow of body fluid through said lumen.

11. The vascular graft of claim 10 wherein said graft is an aneurysm exclusion device and wherein said graft material has a sufficiently low permeability so that when placed over an aneurysm said material substantially excludes the aneurysm from blood flow.

12. An endoluminal prosthesis comprising:
   a tubular graft including a monofilament graft material, a proximal portion having a proximal opening, and a distal portion having a distal opening, said openings and said graft material forming a lumen for the flow of body fluids through said lumen;

wherein said graft material has an average pore size of about 11 microns or less.

13. The endoluminal prosthesis of claim 12 wherein said endoluminal prosthesis further comprises an expandable annular support means for engaging said proximal and distal portions to an inner wall of a body lumen.

14. The endoluminal prosthesis of claim 12, wherein said graft material has a sufficiently low permeability to body fluids so that said lumen is substantially leak-resistant to the body fluids flowing therethrough.

15. The endoluminal prosthesis of claim 12 wherein said graft material has a percent open area of about 1 percent or less.

16. The endoluminal prosthesis of claim 12 wherein said graft material has a substantially uniform wall thickness of about 80 microns or less.

17. The endoluminal prosthesis of claim 12 wherein said prosthesis is a covered stent.

18. The endoluminal prosthesis of claim 13, wherein said prosthesis is an aneurysm exclusion device and said support means comprises a spring means biased in a radially outward direction.

19. The endoluminal prosthesis of claim 13, wherein said proximal portion comprises a trunk portion and said distal portion is branched into at least two branch portions, each of said at least two branch portions having a distal opening, said trunk portion and said branch portions forming a lumen for the flow of body fluids from said proximal opening through said distal openings of said at least two branch portions, and wherein said annular support means comprises an expandable annular spring means biased in a radially outward direction for engaging said proximal and distal portions of said graft to an inner wall of a body lumen.

20. An endoluminal prosthesis comprising:

a tubular graft including a monofilament graft material, a proximal portion having a proximal opening, and a distal portion having a distal opening, said openings and said graft material forming a lumen for the flow of body fluids therethrough;

an expandable annular support means for engaging said proximal and distal portions to an inner wall of a body lumen;

wherein said graft material has an average pore size of about 11 microns or less and a percent open area of about 5 percent or less.

21. The endoluminal prosthesis of claim 20 wherein said graft material has a substantially uniform wall thickness of about 80 microns or less.

* * * * *

UNITED STATES PATENT AND TRADEMARK OFFICE
CERTIFICATE OF CORRECTION

PATENT NO. : 6,344,052 B1
DATED : February 5, 2002
INVENTOR(S) : Greenan et al.

Figure 2:
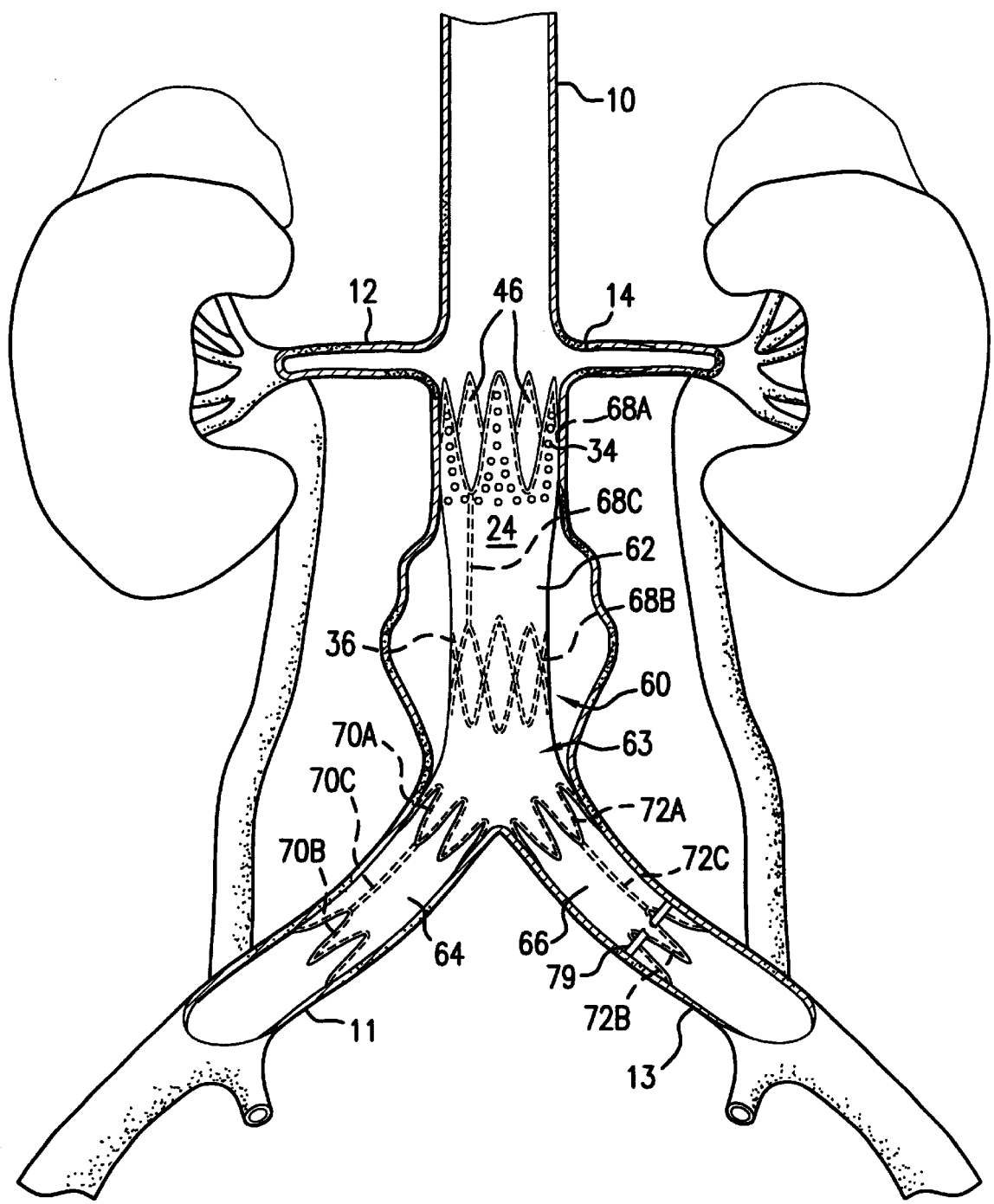
FIG. 2 is an elevational view showing a bifurcated graft of the present invention fully deployed within an aorta and lateral iliac vessels joined therewith.

It is certified that error appears in the above-identified patent and that said Letters Patent is hereby corrected as shown below:

Column 6,
Line 7, "400 ml/cml/min" should read -- 400 ml/cm/min --;

Column 7,
Line 37, "FIG. 4" should read -- FIG. 2 --; and

Column 8,
Line 35, "2300 m/cm$^2$/min" should read -- 2300 ml/cm$^2$/min --.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,344,052 B1                                              Page 1 of 1
DATED         : February 5, 2002
INVENTOR(S)   : Greenan et al.

It is certified that error appears in the above-identified patent and that said Letters Patent is hereby corrected as shown below:

<u>Title page,</u>
Item [56], under References Cited, U.S. Patent No. 5,713,917 should be added.

Signed and Sealed this

Twenty-third Day of December, 2003

JAMES E. ROGAN
*Director of the United States Patent and Trademark Office*